United States Patent [19]

Strumpf et al.

[11] Patent Number: 4,983,207

[45] Date of Patent: Jan. 8, 1991

[54] FUNGICIDES AND PLANT-GROWTH CONTROLLING AGENTS

[75] Inventors: Thomas Strumpf, Potsdam; Horst Lyr, Eberswalde; Dieter Zanke, Potsdam-Babelsberg; Gerlinde Zollfrank nee Baumann, Potsdam, all of German Democratic Rep.; Gyula Oros; Ferenc Virányi, both of Budapest, Hungary; Tibor Ersek, Columbia, Mo.

[73] Assignee: Chinoin Gyogyszer Es Vegyeszeti Termekek Gyara R.T., Budapest, Hungary

[21] Appl. No.: 835,608

[22] Filed: Mar. 3, 1986

[30] Foreign Application Priority Data

Mar. 4, 1985 [DD] German Democratic Rep. ... 273728

[51] Int. Cl.$^5$ ..................... A01N 43/80; A01N 43/84
[52] U.S. Cl. .......................................... 71/88; 71/90; 71/111; 514/471; 514/472; 514/473; 514/445; 514/231.2; 514/380; 514/376; 514/377
[58] Field of Search ............................. 71/88; 514/227

[56] References Cited

U.S. PATENT DOCUMENTS 3,686,399  8/1972  Sanne et al. ..................... 514/227

FOREIGN PATENT DOCUMENTS 0140412  8/1978  Fed. Rep. of Germany ...... 514/227
3321712  6/1983  Fed. Rep. of Germany ...... 514/227

OTHER PUBLICATIONS

LAB 149 202F, A New Funigicide for the Control of Plant Diseases Caused by Oomycetes, E. Ammermann et al, pp. 431–436, BASF Agricultural Research Station, Limburgerhof, West Germany.

*Primary Examiner*—Glennon H. Hollrah
*Assistant Examiner*—Amelia A. Owens
*Attorney, Agent, or Firm*—Herbert Dubno; Jonathan Myers

[57] ABSTRACT

The invention relates to synergistic antifungal and plant-growth regulating compositions and to their application in plant-protection.

The fungicides according to the invention contain the mixture of fungicide from the group of morpholines and acylalanines as active ingredients.

1 Claim, No Drawings

FUNGICIDES AND PLANT-GROWTH CONTROLLING AGENTS

The invention relates to antifungal and plant-growth controlling compositions and to their application in plant-protection.

Alkylmorpholines are put into action to fight the true powdery mildew fungi (DE 11 64 152, DE 11 98 125, DD 140 412, DE 26 56 747). Acylanilines have found entrance as Ocmycete-active fungicides into the practical plant-protection (see R. Wegler, Chemie der Pflanzenschutzund Schadlingsbekampfungsmittel, Band 6).

Based on the relatively narrow action-spectrum of all these compounds different propositions of advantageous mixtures for morpholine fungicides (DD 134 040, DD 104 416, DD 111 014, DD 116 3B4, DD 121 013, De 26 33 874, DE 27 07 709, DE 27 1B 721, DE 28 35 253, DD 155 481, DD 157 592) and acylanilines too (EP 26 873, DE 30 21 06S, GB 2 017 496, JP 1 82 12B 609, EP 30 570, DE 33 01 281) became known.

Nevertheless for some applications the action intensity and the fungicide spectrum could be improved.

The object of the present invention is to find suitable combination-partners for morpholine-fungicides which lead to an increase of the fungicide activity, and inhibit the development of resistance and simultaneously control the fungal growth through an intervention in the metabolism.

It was found, that a mixture consisting of a fungicide from the group of morpholines (A) N-tridecyl-2,6-dimethylmorpholine (Tridemorph) (1); N-cyclodecyl-2,6-dimethylmorpholine (Dodemorph) (2); N-alkyl($C_{12}$)-2,6-dimethylmorpholine (Aldimorph) (3); 4-(3-p-tert.-butylphenyl)-2-methylpropyl)-2,6-cis-dimethylmorpholine (Fenpropemorph) (4) as well as their plantphysiologically acceptable salts, molecular- and addition compounds and one of the following fungicides (B) N-(2,6-dimethylphenyl)-N-furoyl-(2)-alaninemethylester (Furalaxyl) (5); N-(2,6-dimethylphenyl)-N-chloroacetyl-alaninemethylester (CGA 29 212) (6); N-(2,6-dimethylphenyl)-N-phenylacetyl-alaninemethylester (Benalaxyl) (7); 2-chloro-N-(2,6-dimethylphenyl)-N-(tetrahydro-2-oxo-3-furanyl)-acetamide (Ofurace) (8); 3-chloro-N-(tetrahydro-2-oxo-3-furanyl)-cyclopropanecarboxanilide (Cyprofuram) (9); 2-methoxy-N-(2-oxo-1,3-oxazolidin-3-yl)-N-(2,6-dimethyl-phenyl)-acetamide (Oxadixyl) (10); N-isoxazol-5-yl-N-(2,6-xylyl)-alaninemethylester (LAB 149 202 F) (11); N-(2 6-dimethylphenyl)-2-methoxy-N-(tetrahydro-2-oxo-3-furany)-acetamide (RE 26 745) (12); N-(2,6-dimethylphenyl)-2-methoxy-N-(tetrahydro-2-oxothien-3-yl)-acetamide (RE 26 940) (13), as active ingredients, possesses an improved fungicide activity especially against OOmycetes and is suitable for the control of plant-growth. The effects induced by the combination of the active agents are based on synergistic influences. The increased practical breadth of application of the new combinations is advantageous, which makes e.g. possible to control the downy and powdery mildews. Moreover the probability of the appearance of resistant branches, because of the different mode of action of the two components and the differences in sensitivity of the stages of fungal life cycle, markedly decreased. The mixtures according to the invention this way represent an enrichment of the prior art.

With the new combination the damaging fungi appearing on plants or on the parts of plants can be fighted down. Based on the systemic properties of both components even new growing parts of plants will be protected against fungal attacks. The mixtures are efficacious against phytopathogenic fungi of the following groups: Assomycetes (e.g. Erysiphe- and Sclerotinia-varieties), Oomycetes (firstly Phytophthora-, Peronospora- and Plasmopara-varieties) and Basidiomycetes (e.g. Rhizoetonia-varieties).

The combinations are employed advantageously for the control of plant-growth of cereals, vegetables and vegetable cultures as e g. cucumbers, tomato, sun flowers, among others of cultivataed plants as well as of some ornamental plants. At the employed concentrations no phytotoxic damages were observed. The seed corn's quality will not be affected disadvantageously. Further, the fungicide effect of the components of the combinations is of importance for the safeguarding of the yield.

The mass ratio of the morpholine-fungicides and fungicides of the second group in the mixtures can be varied, between 20 : 1 to 1 : 2, especially from 20 : 1 to 1 : 1, advantageously from 10 : 1 to 2 : 1, preferred from 5 : 1 to 3 : 1.

The preparation of the enumerated morpholines (A) inclusive that of its salts, molecular and addition compounds (DE 11 64 152, DE 11 73 722, DE 24 61 513, DE 11 98 125, DD 140 041, DE 26 56 747), as well as of the other known fungicides (B) (DE 25 13 78B, DE 23 50 944, DD 142 042, US 3 933 860, DE 27 24 786, Fr 2 463 132, EP 26 873, DE 28 41 824, BE S71 668) is well known.

The combinations of the active ingredients according to the invention can be transferred into usual formulations as solutions, emulsion concentrates, suspensions, powders, spray powders, strewing powders, pastes, granulates, aerosols, seed corn powder etc. The formulations will include the active ingredients and can include surface active agents, solid or liquid diluents or solvents, liquefied gases under pressure and other materials as required to produce the desired formulation. The formulations are prepared by methods known per se.

Liquid solvents can be e.g.: fractions of mineral oils with a mean to high boiling point, e.g. kerosin or Diesel-oil, oils of plant or animal origin, aliphatic, cyclic and aromatic hydrocarbons, e.g. toluene, xylene, alkylated naphtalenes, cyclohexanes, paraffin, alkohols, glycols, esters, ketones and halogenated hydrocarbons, e.g. butanol, ethyleneglycol, methylethylketone, cyclohexanone, chloroform, chlorobenzene or polar solvents, e.g. dimethylformamide, dimethylsulfoxide or N-methylpyrrolidone.

As liquefied gases under pressure aerosol gases are meant e.g. halogenated hydrocarbons, propane, butane and carbon dioxide. As solid carriers natural rock fluors, e.g. kaoline, talc, silica, montmorillonite and diatomaceous earth and synthetic rock flours, e.g. highly dispersed silicic acid, aluminium-oxide and silicates can be applied. For granulates the following materials are suitable as carriers: broken natural stones, e.g. calcite, marble, pumice-stone, dolomite, synthetic granulates from inorganic and organic flours as well as granulates from organic material, e.g. sawdusts, shells of coconut, corn-cobs and tobacco stems.

The surface-active agents act as wetting eumlsifying and/or dispersing agents. Here the following compounds can be taken in consideration: alkali-, earth alkali- and ammonium salts of ligninsulphonic acid, naphthalinesulphonic acid, phenolsulphonic acid, alkylarylsulphonates, alkylsulphates, alkylsulphonates, alkali- and earth alkali salts of dibuthylnaphthalenesulphonic-acid, laurylethersulphate, fatty alcohol sulphates, alkali- and earth alkali salts of fatty acids, salts of sulphated hexadecanols, heptadecanols, octadecanols, salts of sulphated fatty alcohol glycolethers, condensation products of sulphonated naphthalenes and naphthalene derivatives with formaldehyde, condensation products of naphthalenes of the naphthalenesulphonic acids respectively with phenol and formaldehyde, polyoxyethylene-octyl-phenolether, ethoxylated isooctylphenol, octylphenol, nonylphenol, alkylphenolpolyglicolether, tributhylphenylpolyglycolether, alkylarylpolyether alcohols, isotridecyl alcohol, fatty alcohol ethyleneoxyde-condensates, ethoxylated Rizinus-oil, polyoxyethylenealkylether, ethoxylated polyoxypropylene, aurylalcoholpolyglycolether-acetal, sorbitester, lignin, sulphite waste alkalis and methyl cellulose.

The formulations may further contain adhesion agents as carboxy methylcellulose, natural or polymers as gum arabic, polyvinylalcohol or polyvinylacetate and the like.

The formulations contain generally 1 to 95% mass of the active ingredients (A) +(B).

Aqueous forms of application can be prepared from emulsion concentrates, suspensions, spray powders (strewing powders) etc. by addition of water. The preparation of emulsions or oil dispersions is carried out by dissolving the active ingredients and other additives in oil or a solvent or homogenization in water by means of wetting-, dispersing- or emulgeating agents.

The application occurs in usual manner, e.g. by immersion, pouring, spraying, strewing or dusting. The applied quantities depend on the specific goal of application and generally lie between 0.5 and 5.0 kg/ha respectively 10–200 g active ingredient per 100 kg seed corn. The active agent combinations according to the invention can be mixed for the enlargement of the application breadth and plant protection with other known fungicides, herbicides, insecticides, desiccants, defoliants: growth controlling agents or fertilizers.

EXAMPLE 1

Composition of a springling powder
18 mass% of Tridemorph
7 mass% of LAB 149 202 F
5 mass% of calciumligninsulphonate
5 mass% of alkylphenol-ethyleneoxide addition agent
20 mass% of silicic acid
45 mass% of kaolin

EXAMPLE 2

Composition of an emulsion-concentrate
35 mass% of Aldimorph
15 mass% of Ofurace
18,5 mass% of toluene
18,5 mass% of cyclohexanone
10 mass% of tert. butanol
2 mass% of epoxydated octylphenolether
1 mass% of Tween 20...80

EXAMPLE 3

Synergistic effect of mixtures from morpholine-fungicides (A) and fungicides (B) on Phytophthora cinnamomi in vitro Phytphthora cinnamomi was grown in Petri dishes on green pea agar media containing the mentioned active agents, combinations respectively in the given concentrations. The inoculation was carried out with mycelial discs. After 5 days of cultivation at 21° C. the colony diameter was measured and the inhibiton of the radial growth related to the untreated control was calculated. The synergistic effect was calculated according to COLBY.

| Active agent, combination resp. | Concentration (mg/l) | Growth inhibition (%) | Effect according to COLBY (%) |
| --- | --- | --- | --- |
| Tridemorph (1) | 4 | 51 | — |
|  | 0.4 | 6 | — |
|  | 0.04 | 1 | — |
| Dodemorph (2) | 40 | 52 | — |
|  | 4 | 12 | — |
|  | 0.4 | 2 | — |
| Aldimorph (3) | 40 | 64 | — |
|  | 4 | 1 | — |
|  | 0.4 | 1 | — |
| Aldimorph HCl (3a) | 40 | 81 | — |
|  | 4 | 24 | — |
|  | 0.4 | 3 | — |
| Fenpropemorph HCl (4a) | 4 | 1 | — |
|  | 0.4 | 1 | — |
| Fenpropemorph-methosulphate (4b) | 0.4 | 3 | — |
|  | 0.04 | 2 | — |
| Furalaxyl (5) | 1 | 69 | — |
|  | 0.1 | 19 | — |
|  | 0.01 | 2 | — |
| Benalaxyl (7) | 10 | 40 | — |
|  | 1 | 19 | — |
|  | 0.1 | 6 | — |
| Ofurace (8) | 10 | 56 | — |
|  | 1 | 20 | — |
|  | 0.1 | 5 | — |
| Cyprofuram (9) | 10 | 68 | — |
|  | 1 | 14 | — |
|  | 0.1 | 1 | — |
| LAB 149 202 F (11) | 10 | 84 | — |
|  | 1 | 25 | — |
|  | 0.1 | 2 | — |
| RE 26 745 (12) | 1 | 77 | — |
|  | 0.1 | 12 | — |
|  | 0.01 | 2 | — |
| 1 + 5 | 4 + 1 | 88 | +3 |
|  | 0.4 + 0.1 | 49 | +25 |
|  | 0.04 + 0.01 | 12 | +9 |
| 1 + 11 | 4 + 1 | 77 | +14 |
|  | 0.4 + 0.1 | 17 | +9 |
| 2 + 7 | 40 + 10 | 97 | +26 |
| 2 + 8 | 4 + 1 | 45 | +15 |
|  | 0.4 + 0.1 | 28 | +21 |
| 2 + 9 | 40 + 10 | 100 | +15 |
| 2 + 12 | 0.4 + 0.1 | 32 | +17 |
| 3 + 5 | 4 + 1 | 78 | +9 |
| 3 + 8 | 4 + 1 | 34 | +14 |
| 3 + 11 | 4 + 1 | 53 | +27 |
| 3a + 7 | 4 + 1 | 76 | +38 |
|  | 0.4 + 0.1 | 17 | +8 |
| 3a + 12 | 0.4 + 0.1 | 21 | +7 |
| 4a + 5 | 4 + 1 | 73 | +4 |
|  | 0.4 + 0.1 | 22 | +2 |
| 4b + 5 | 0.4 + 0.1 | 38 | +16 |
|  | 0.04 + 0.01 | 15 | +11 |

EXAMPLE 4

Synergistic curative effect of mixtures from morpholine (A) and acylalanine (B) fungicides on Plasmopara halstedii downy mildew of sunflower Sunflower germs (Helianthus ammus cv. GK-70) were infected with a suspension of zoospores of Plasmopara halstedii (2.5×10⁵ cell)ml). After 24 hours the seedlings were immersed into the aqueous solutions (emulsions) of various concentrations of the mentioned substances (from 50 EC) for 18 hours.

After 14 days the percent ratio of the infected plants was determined and the $ED_{50}$ value was calculated. The significance for a synergistic effect was expressed as Co T. I. and calculated according to the following equation:

$$Co\ T.I. = \frac{\frac{1}{ED_{50}\ Mixt}}{\frac{a}{ED_{50}\ A} + \frac{b}{ED_{50}\ B}}$$

In this equation a and b are indicating the current mass parts of the active agents A and B in the mixture. A Co I. I. value >1.25 means, that a significant synergism was present.

| Active agent resp. combination | $ED_{50}$ (mg/l) | Co T.I. |
|---|---|---|
| Aldimorph (3) | 1040.0 x/ | — |
| Aldimorph HCl (3a) | 771.0 x/ | — |
| RE 26745 (12) | 33.0 | — |
| 3 + 12 (3 + 1) | 5.4 | 5.57 |
| 3a + 12 (3 + 1) | 16.1 | 1.82 | x/phytotoxic

EXAMPLE 5

Synergistic effect of mixtures from morpholine (A) and acylalanine (B) fungicides on the vegetative growth of some Phytophthora species in vitro The fungi were—as described in Example 3—grown on green-pea agar plates containing the active ingredients. The $ED_{50}$ values were calculated based on the inhibition of the radial growth comparing to the untreated control. The mixing ratio in all of the cases was 4:1 mass parts. The synergistic effect was expressed as Co T. I. according to Example 4, where values from 1.0±0.25 are meaning an additive effect, and those from >1.25 a significant synergistic effect.

| Combination | P. cactorum $ED_{50}$ (Co T.I.) (mg/l) | P. cambivora $ED_{50}$ (Co T.I.) (mg/l) |
|---|---|---|
| Tridemorph (1) | 24.2 | 12.4 |
| Dodemorph (2) | 47.3 | 258.0 |
| Aldimorph (3) | 32.7 | 36.2 |
| Aldimorph HCl (3a) | 34.6 | 23.6 |
| Fenpropemorph (4) | 175.0 | 6.41 |
| Furalaxyl (5) | 0.17 | 0.05 |
| Benalaxyl (7) | 1.8 | 0.25 |
| Ofurace (8) | 0.79 | 1.12 |
| Cyprofuram (9) | 5.0 | 2.8 |
| Oxadixyl (10) | 0.12 | 0.45 |
| LAB 149 202 F (11) | 0.15 | 0.08 |
| RE 26 940 (13) | 0.22 | 0.31 |
| 1 + 10 | 0.19 (0.62) | 0.10 (3.93) |
| 1 + 11 | 0.09 (1.63) | 0.73 (0.11) |
| 2 + 10 | 0.02 (5.94) | 0.09 (4.97) |
| 3 + 5 | 0.11 (1.51) | 0.07 (0.71) |
| 3 + 7 | 1.22 (1.21) | — |
| 3 + 8 | 1.37 (0.53) | 0.75 (1.33) |
| 3 + 9 | 2.3 (1.35) | 2.4 (0.89) |
| 3a + 9 | 1.4 (2.26) | 0.91 (2.09) |
| 3a + 13 | 0.27 (0.80) | — |
| 4 + 10 | 0.02 (5.98) | 0.22 (1.60) |

| Active agent, combination resp. | P. citricola | P. parasitica var. nicotianae |
|---|---|---|
| Tridemorph (1) | 3.9 | 56.7 |
| Dodemorph (2) | 36.9 | 124.3 |
| Aldimorph (3) | 32.5 | 517.6 |
| Aldimorph HCl (3a) | 11.0 | 162.9 |
| Fenpropemorph (4) | 29.9 | 142.7 |
| Furaxyl (5) | 0.21 | 0.21 |
| Benalaxyl (7) | 6.1 | 5.5 |
| Ofurace (8) | 6.84 | 14.26 |
| Cyprofuram (9) | 32.0 | 9.9 |
| Oxadixyl (10) | 0.49 | 0.13 |
| LAB 149 202 F (11) | 0.34 | 0.16 |
| RE 26 940 (13) | 1.67 | — |
| 1 + 10 | 0.32 (0.93) | 0.24 (0.54) |
| 1 + 11 | — | — |
| 2 + 10 | 0.15 (3.10) | 0.09 (1.44) |
| 3 + 5 | 3.11 (0.07) | 1.23 (0.17) |
| 3 + 7 | 1.58 (2.21) | 1.36 (3.88) |
| 3 + 8 | 0.85 (4.37) | 5.15 (2.49) |
| 3 + 9 | 7.4 (0.88) | 9.6 (0.96) |
| 3a + 9 | 1.69 (1.50) | 3.2 (2.69) |
| 3a + 13 | 0.78 (1.33) | — |
| 4 + 10 | 2.62 (0.18) | 0.19 (0.68) |

EXAMPLE 6

Inhibition of the epicotyl longation of soy-bean Glycine max by mixtures from morpholine (A) and acylalanine (B) fungicides (immersion of the seed)

Soy-bean seeds c.v. (harosoy) were dressed with the agents in the given quantity of application and one week after treatment they were sowed (50 seeds of each application). After three weeks the length of epicotyl was measured.

| Active agent, combination resp. | Concentration (g 100 kg of seeds) | Length of the epicotyles (mm) | Difference comp. to the control (mm) | Effect according to COLBY |
|---|---|---|---|---|
| untreated control | — | 147 | — | — |
| Tridemorph-methosulphate | 40 | 122 | −25 | — |
| Fenpropemorph methosulphate (4b) | 40 | 39 | −108 | — |
| Benalaxyl (7) | 10 | 151 | +4 | — |
| LAB 149 202 F (11) | 10 | 140 | −7 | — |
| RE 26 745 (12) | 10 | 155 | +8 | — |
| 1b + 11 | 40 + 10 | 86 | −61 | 31 |
| 1b + 12 | 40 + 10 | 111 | −36 | 21 |
| 4b + 7 | 40 + 10 | 32 | −115 | 15 |
| 4b + 12 | 40 + 10 | 18 | −129 | 38 |

EXAMPLE 7

Growth control of tomato-plants Solanum lycopersicum by mixtures of morpholine (A) and acylalanine (B) fungicides The enumerated active agents were formulated one by one and in combination as 25 WP, suspended in water and sprayed run off on tomato plants (c.v. Harzfeuer) in the four-leaf stage (20 plants in each application) After cultivation during 12 days in a green-house the dry-mass was determined and compared with that of the untreated control.

| Active agent, combination resp. | conc. (mg/l) | dry-mass (g) | increase of the dry-mass (%) |
|---|---|---|---|
| Untreated control | 0 | 1.36 | 100 |
| Tridemorph (1) | 0.1 | 1.48 | 109 (−) |
| Tridemorph HCl (1a) | 0.1 | 1.56 | 115 (−) |

-continued

| Active agent, combination resp. | conc. (mg/l) | dry-mass (g) | increase of the dry-mass (%) |
|---|---|---|---|
| Aldimorph (3) | 0.1 | 1.51 | 111 (−) |
| Aldimorph HCl (3a) | 0.1 | 1.53 | 112 (−) |
| Fenpropemorph (4) | 0.1 | 1.53 | 112 (−) |
| Fenpropemorph HCl (4a) | 0.1 | 1.50 | 110 (−) |
| Ofurace (8) | 0.05 | 1.33 | 98 (−) |
| Cyprofuram (9) | 0.05 | 1.32 | 97 (−) |
| LAB 149 202 F (11) | 0.05 | 1.39 | 102 (−) |
| RE 26 745 (12) | 0.03 | 1.44 | 106 (−) |
| 1 + 12 | 0.1 + 0.03 | 1.65 | 121 (+) |
| 1a + 12 | 0.1 + 0.03 | 1.58 | 116 (+) |
| 3 + 8 | 0.1 + 0.05 | 1.66 | 122 (+) |
| 3 + 9 | 0.1 + 0.05 | 1.64 | 121 (+) |
| 3 + 11 | 0.1 + 0.05 | 1.63 | 120 (+) |
| 3 + 12 | 0.1 + 0.03 | 1.66 | 122 (+) |
| 3a + 12 | 0.1 + 0.03 | 1.78 | 131 (+) |
| 4 + 12 | 0.1 + 0.03 | 1.66 | 122 (+) |
| 4a + 12 | 0.1 + 0.03 | 1.68 | 123 (+) |

(+)Difference to the control is significant (Pi = 5%)
(−)Difference to the control is not significant (Pi < 5%)

What we claim is:

1. A fungicidal composition effective against Phytophthora Cinnamomi and effective in regulating plant growth containing as active ingredients:
N-alkyl ($C_{12}$)-2,6-dimethylmorpholine; and
N-isoxazol-5-yl-N-(2,6-xylyl)-alanine methyl ester; in a weight ratio of 4:1, together with a fungicidally acceptable inert carrier.

* * * * *